United States Patent [19]

Herzog et al.

[11] 3,954,974

[45] May 4, 1976

[54] DISINFECTANT FOR THE SURFACE OF HUMAN BODY PARTS CONTAINING HYDROGEN PEROXIDE

[76] Inventors: Paul Herzog; Karin Herzog-Thomander, both of Avenue de Rolliez 10, Vevey, Switzerland

[22] Filed: July 30, 1974

[21] Appl. No.: 493,147

Related U.S. Application Data

[63] Continuation-in-part of Ser. No. 365,681, May 31, 1973, abandoned.

[30] Foreign Application Priority Data

June 9, 1972   Switzerland.......................... 8641/72

[52] U.S. Cl................................. 424/130; 424/170
[51] Int. Cl.$^2$.................... A61K 33/40; A61L 13/00
[58] Field of Search ............ 424/130, 168, 170, 172

[56] References Cited
UNITED STATES PATENTS 2,886,532   5/1959   Richmond et al. ................. 252/104

3,639,574   2/1972   Schmouka .......................... 424/130

OTHER PUBLICATIONS

Sagarin, "Cosmetics, Science & Technology," pp. 1004–1008 (1957).

Remmington, Practice of Pharmacy, 13 Ed. 1965, pp. 527–537.

Chemical Abstracts 68:24515b (1968).

*Primary Examiner*—Leonard Schenkman
*Attorney, Agent, or Firm*—Young & Thompson

[57] ABSTRACT

A disinfectant which is an aqueous emulsion of hydrogen peroxide of the oil-in-water type. The hydrogen peroxide in this emulsion is more stable and more active than in aqueous solution. The disinfectant may be used for disinfecting doctors', dentists' and surgeons' hands, but also for treating skin diseases, injuries and irritations.

3 Claims, No Drawings

DISINFECTANT FOR THE SURFACE OF HUMAN BODY PARTS CONTAINING HYDROGEN PEROXIDE

This application is a continuation-in-part of our copending application Ser. No. 365,681 filed May 31, 1973 and now abandoned.

The present invention relates to disinfectants. The disinfectant of the invention is particularly useful for the disinfection of doctor's hands, especially surgeon's hands.

Disinfectants are known which contain mercury in chemically bonded form, or chlorinated organic substances like hexachlorophene. The use of mercury containing and chlorinated substances has, however, been questionable for some time, and it is contemplated to forbid them completely if they are not already prohibited for use in disinfectants.

A further well known disinfectant is ethanol but aqueous ethanol solutions having an ethanol concentration of about 70 to 80% can only be used exceptionally since they desiccate the human skin too extensively.

Aqueous solutions of hydrogen peroxide have already been proposed and used as a disinfectant. Such solutions, however, suffer from the drawback that they are unstable. Furthermore, they are difficult or impossible to apply. If these solutions did not have these drawbacks, hydrogen peroxide would be an ideal disinfectant. It destroys harmful microorganisms not by intoxication but by oxidation. After use, it remains in the form of water. However, the instability of aqueous hydrogen peroxide and its difficult or impossible application have rendered until now its use for the disinfection of parts of the body, especialy or surgeon's hands, impossible. Hydrogen peroxide emulsions of the water-in-oil type are known. The hydrogen peroxide is dissolved in microscopical spherical water drops which constitute the dispersed phase. Each drop is surrounded by the continuous oil phase, and thus the hydrogen peroxide is perfectly protected from contact with air or other compounds or materials. But the hydrogen peroxide is so well protected, that it is not only stabilized but also prevented from acting on the surface of a human body part in order to disinfect it. It follows that such known emulsions of the water-in-oil type cannot be used for disinfecting human body parts, such as surgeons' hands. It is quite significant that such known emulsions are used for bleaching fabrics, where conditions exist which are quite different from those occurring in disinfecting the surface of a human body part.

Contrary to what is known from the prior art, our emulsion is of the oil-in-water type, i.e., the hydrogen peroxide is in the continuous phase. It is surprising that in this case the hydrogen peroxide is sufficiently stable for storing without decomposition over a reasonable time, but still sufficiently active for disinfecting the surface of a human body part within a very short time. Anyone skilled in the art would expect that hydrogen peroxide in the continuous phase will readily decompose in contact with air or with the walls of a container, as no protection is present. One would also expect that if, surprisingly and against common knowledge, the hydrogen peroxide would really be stable in such an emulsion, it would not act as a disinfectant in a reasonably short time. Thus, our discovery is the contrary of what anyone skilled in the art would expect.

The main object of the invention is to provide a disinfectant which fulfils the four principal requirements of a disinfectant namely:
reliable and immediate disinfection,
avoiding the formation of resistant bacterium and virus strains,
avoiding adversely affecting of sewage waters after use, and
good compatibility with the skin and body tissues.

These and other objects are accomplished by the disinfectant of the invention, consisting essentially of an oil-in-water emulsion having a continuous aqueous phase containing an amount of hydrogen peroxide effective to disinfect human body part upon contact. It is possible to use all appropriate emulsifiers and other additives. The concentration and the nature of the emulsifiers and other ingredients will generally be selected such that the emulsion is stable and may be stocked. It is not important if the emulsion breaks on contact with the skin or the tissue. It is to be supposed that the emulsion when applied to the hands is at least in part massed against and into the skin during the washing movements, becoming thereby unstable and liberating hydroperoxide with a maximum of activity.

It has been found that hydrogen peroxide is much more active in the emulsions of the invention than in the form of a normal aqueous solution at the same concentration. In order to achieve a predetermined disinfecting effect, less hydrogen peroxide is necessary when using a composition of the invention than with a conventional aqueous solution thereof used in the past. It is not possible to give a simple explanation of this fact.

After being used, the emulsion may be removed by drying or by rinsing with water.

The time period necessary for the disinfection of surgeon's hands, about 2 to 6 minutes, may be varied by nature and concentration of the emulsifier, by the concentration of the hydrogen peroxide, and by additives which lower the surface tension and have themselves an additional disinfecting activity, like alcohol. As an alcohol, e.g. methanol, ethanol, glycol or glycerol may be used. After rubbing the disinfectant into the hands, it may easily be removed by washing with water, the hands remaining disinfected.

Upon dissolving hydroperoxide in the aqueous phase of an emulsion, it is stabilized and does not decompose on storage, even in open containers and at elevated temperatures.

Although the specified emulsions are sufficiently stable per se, known hydrogen peroxide stabilizers may optionally be added, like urea.

The oil phase may be constituted by any suitable hydrophobic organic substance. Examples thereof are glycol mono, di and triesters of fatty acids, paraffins of different consistency, higher alcohols and petroleum jelly such as Vaseline. The emulsifier is suitably selected as being compatible with the skin and the tissue.

All of the compounds of the disinfectant are preferably selected such that no allergic reactions occur. For the sake of safety it has been found suitable to add an antiallergenic to the disinfectant, like an azulene, e.g. guajazulene. The latter is distributed commercially as an aqueous "solution", i.e. a finely dispersed emulsion, having a concentration of about 25% by weight.

The preparation of the novel disinfectant is very easy and is performed by operations known per se. The different compounds may be added in any sequence. The hydrogen peroxide is preferably added in such a concentration which permits one to obtain the desired final concentration.

The oil phase is preferably a mixture comprising from 80 to 320 parts by weight of glycerol monostearate, from 80 to 320 parts by weight of paraffin oil, from 80 to 320 parts by weight of cetyl alcohol, from 150 to 600 parts by weight of petroleum jelly such as Vaseline, and from 10 to 200 parts by weight of polyoxyethylene derivatives of anhydrosorbitols partially esterified with a fatty acid, e.g. polyoxyethylene sorbitan mono-oleate ("Tween 80").

One liter of this base may be mixed at 70° to 80°C with 3 to 7 liters of water of about the same temperature, containing 0.4 to 5 grams of an azulene, especially guajazulene. To this mixture, 100 to 450 g of hydrogenperoxide, dissolved in water, are added warm or cold, a stabilizer for hydrogenperoxide, like urea, being optionally present.

The following examples are illustrative only and are not to be construed to limit the invention.

EXAMPLE 1

On a water bath, the following ingredients are mixed, using a conventional stirring apparatus: 160 g of glycerol monostearate, 160 g of paraffin oil, 160 g of cetyl alcohol, 300 g of Vaseline brand petroleum jelly, 50 g of "Tween 80" (polyoxyethylene sorbitan mono-oleate) and 170 g of water.

300 g (about 350 ml) of the base so obtained are mixed with one liter of water at about 80°C, containing 3 g of a 25% aqueous solution of guajazulene. Furthermore, 800 ml of water are added containing 200 ml of 30% hydrogenperoxide.

The disinfectant so obtained presents all the desirable properties discussed above. Instead of 200 to 450 g of water in 1 liter thereof, one may use about 200 to 450 g of ethanol in order to further shorten the cleaning time.

A disinfectant for surgeons contains preferably about 60 g $H_2O_2$ per liter of the total composition, and about 40% of the water may be replaced by ethanol.

EXAMPLE 2

48 g of glycerol monostearate, 48 g of paraffin oil, 48 g of cetyl alcohol, 90 g of Vaseline, 14 g of "Tween 80", 1782 g of water, 3 g of a 25% aqueous solution of guajazulene and 268 g of a 30% aqueous hydrogenperoxide solution are heated together to 80°–90°C. The mixture is allowed to cool to room temperature on a water bath under stirring, and a disinfectant ready fur use is obtained containing 3.5% by weight of hydrogen peroxide. This mixture does not contain any preserving agent.

In Examples 1 and 2, the emulsifier ("Tween 80") amounts to about 0.7 to 0.8% by weight. This amount may be varied depending on the desired stability of the emulsion, the lower limit being about twice or even four times this basic amount. If other emulsifiers are used, corresponding amounts will be selected, and conveniently such amounts that equal approximately the emulsifying ability of the mentioned "Tween 80" amounts.

The stability of the emulsion may be limited more or less by, e.g., selecting the concentration of "Tween 80" lower than 0.75%, lower than 0.35% or even lower than 0.15%. Other emulsifiers than "Tween 80" will be used with corresponding concentrations for achieving a corresponding stability.

The presence of a particular emulsifier is not always necessary. For example, it is possible that a component of the oil phase is sufficiently emulsifying.

When a disinfectant is to be used which is stabilized to a high degree, e.g. by a high amount of emulsifier in order to obtain a long storage time, it may be convenient to treat the hands to be disinfected with an emulsion breaking agent before using the emulsion. All known emulsion breaking agents may be used for this purpose, e.g. soap or calcium or aluminium ions.

EXAMPLE 3

Using the method of Example 2, 6 g of bleached bee wax, 4 g of cetyl alcohol, 25 g of anhydrous lanoline, 25 g of white Vaseline oil, 10 g of 30% hydrogen peroxide and 30 g of water are mixed together.

EXAMPLE 4

Using the method of Example 2, 20 g of white Vaseline oil, 20 g of anhydrous lanoline, 6 g of cetyl alcohol, 10 g of 30% hydrogen peroxide and 44 g of water are mixed together.

EXAMPLE 5

Using the method of Example 2, 15 g of cetyl alcohol, 10 g of glycerol, 1 g of sodium laurylsulfate, 10 g of 30% hydrogenperoxide and 84 g of water are mixed together.

EXAMPLE 6

Using the method of Example 2, 1 g of stearyl alcohol, 2 g of solid paraffin, 5 g of stearic acid, 8 g of glycerol monostearate, 1.5 g of liquid paraffin, 0.8 g of triethanolamine, 8 g of glycerol, 10 g of 30% hydrogenperoxide and 63.7 g of water are mixed together.

EXAMPLE 7

The water to be used is prepared by distilling water and adding to the distilled water 0.15% by weight of p-hydroxybenzoic acid methyl ester.

The oil phase is prepared by heating to 120°C in a stainless steel vessel under stirring 230 g of monostearine glyceride, 230 g of paraffine oil, 230 g of cetyl alcohol, and 430 g of Vaseline brand petroleum jelly.

The water phase is prepared in two steps:
a. 5300 g of the water prepared above, 65 g of polyoxyethylenesorbitan mono-oleate, and 10 g of salicylic acid are warmed to 90°C.
b. 2350 g of the water prepared above and 1175 g of an aqueous solution containing 30% hydrogenperoxide are warmed to 40°C.

The oil phase is slowly added under stirring to part a) of the water phase, and the mixture is cooled to 40°C. Part b) of the water phase is added under stirring to the thus obtained mixture. The whole emulsion thus obtained is cooled to room temperature.

In this manner, one obtains about 10 kg of a disinfectant having a pH of 2.8 to 3.0, and a hydrogenperoxide concentration of about 3.5%. The amount of hydrogenperoxide can be varied between about 0.5% and about 12%, by varying the proportion between water and hydrogenperoxide in solution b) above.

Normally, commercially available aqueous solutions containing 30% of hydrogenperoxide are acid and give a pH between about 2.7 and 4.7 for the final disinfectant. This is an advantage, as disinfectants having such an acidity are not only more stable than at higher pH values, but have also a very good compatibility for the human skin. However, in some cases it may be desirable to have higher pH values, such as 5 to 8. In this pH range, the hydrogenperoxide is less stable and thus acts more rapidly for disinfecting the human skin. The pH value can be raised and adjusted to 5 to 8 by adding e.g. mono- or di-sodium phosphate in suitable amounts.

The hydrogenperoxide emulsion of the invention is not only applicable as a disinfectant for doctors and dentists and for general sick-nursing purposes; the emulsion may also be used for the treatment of skin diseases provoked or adversely affected by micro-organisms. In these cases, the emulsion may be combined with corticosteroids and acetyl salicylic acid.

The emulsions of the invention may also be used for intimate hygiene, and in some cases, the activity may be enhanced by adding of an astringent agent.

Furthermore, these emulsions may be used against troubles caused by haemorrhoids or against irritations of the anal opening. In this case, the activity may be enhanced by the addition of aluminum and zinc compounds.

These emulsions may further be used on burns, against skin redness as caused by heat, and cutaneous vesicles.

The disinfectant power of the emulsions of the invention is already very strong. It may, however, by convenient to combine these emulsions with other disinfecting agents like hexachlorophene. It is now known that the latter may be toxic, but it presents certain advantages since it is partially absorbed and is therefore active for a long time. If hexachlorophene or other toxic disinfecting agents are combined with the emulsions of the invention, only very little and thus harmless amounts of the toxic agents are sufficient to achieve a strong effect.

We claim:

1. A disinfectant for the surface of human body parts, consisting essentially of an oil-in-water emulsion having a continuous aqueous phase containing an amount of hydrogenperoxide effective to disinfect human body parts upon contact, the oil phase being the dispersed phase of the emulsion and containing by weight, from 80 to 230 parts of glycerol monostearate, from 80 to 320 parts of paraffin oil, from 80 to 320 parts of cetyl alcohol, from 150 to 600 parts of petroleum jelly and from 10 to 200 parts of a polyoxyethylene derivative of anhydrosorbitol partially esterified with a higher fatty acid, and wherein the total emulsion comprises per liter of said oil phase, a water phase containing from 3 to 7 liters of water and from 100 to 450 g of hydrogen peroxide.

2. A disinfectant as claimed in claim 1, said polyoxyethylene derivative being polyoxyethylene sorbitan mono-oleate and said water containing in solution from 0.4 to 5 g of an azulene.

3. A disinfectant for the surface of human body parts, comprising per 10 kg of total weight, a dispersed oil phase consisting essentially of about 230 g of monostearine glyceride, about 230 g of paraffin oil, about 230 g of cetyl alcohol, and about 430 g of petroleum jelly, and the balance of the disinfectant being a continuous water phase containing about 0.5% to about 12% of hydrogenperoxide and about 0.15% by weight of p-hydroxybenzoic acid methyl ester.

* * * * *